US008487272B2

(12) United States Patent
Tinsley

(10) Patent No.: US 8,487,272 B2

(45) Date of Patent: Jul. 16, 2013

(54) FLUORESCENCE EMISSIONS DETECTOR

(75) Inventor: Kenneth E. Tinsley, Frisco, TX (US)

(73) Assignee: Authentix, Inc., Addison, TX (US)

(*) Notice: Subject to any disclaimer, the term of this patent is extended or adjusted under 35 U.S.C. 154(b) by 398 days.

(21) Appl. No.: 12/967,579

(22) Filed: Dec. 14, 2010

(65) Prior Publication Data

US 2012/0145924 A1 Jun. 14, 2012

(51) Int. Cl.
*G21V 9/16* (2006.01)

(52) U.S. Cl.
USPC .................. 250/458.1; 250/459.1; 250/461.1

(58) Field of Classification Search
USPC ................................ 250/458.1, 459.1, 461.1
See application file for complete search history.

(56) References Cited

U.S. PATENT DOCUMENTS

| | | | | |
|---|---|---|---|---|
| 3,340,978 | A | 9/1967 | Haville | |
| 4,555,177 | A | 11/1985 | Barrett | |
| 5,281,810 | A | 1/1994 | Fooks et al. | |
| 5,498,865 | A | 3/1996 | Gaboury et al. | |
| 5,621,205 | A | 4/1997 | Warner et al. | |
| 5,877,645 | A | 3/1999 | Comino et al. | |
| 6,223,876 | B1 | 5/2001 | Walsh et al. | |
| 7,030,371 | B2 * | 4/2006 | Vasic et al. | 250/271 |
| 7,046,349 | B2 | 5/2006 | Everall et al. | |
| 7,067,824 | B2 | 6/2006 | Muller et al. | |
| 7,220,953 | B2 | 5/2007 | Teo et al. | |
| 7,301,158 | B1 * | 11/2007 | Hoang | 250/458.1 |
| 2003/0178578 | A1 * | 9/2003 | Rao et al. | 250/458.1 |
| 2004/0106211 | A1 * | 6/2004 | Kauer et al. | 436/169 |
| 2006/0054790 | A1 | 3/2006 | Schmidt | |
| 2008/0265177 | A1 * | 10/2008 | Connally et al. | 250/461.2 |
| 2008/0303920 | A1 * | 12/2008 | Kinoshita | 348/226.1 |
| 2009/0051530 | A1 | 2/2009 | Brooks et al. | |
| 2009/0152468 | A1 | 6/2009 | Allen et al. | |
| 2009/0235615 | A1 | 9/2009 | Pinchen | |
| 2009/0255990 | A1 | 10/2009 | Allen et al. | |
| 2011/0064296 | A1 * | 3/2011 | Dixon | 382/133 |

OTHER PUBLICATIONS

The Texas Instruments / Burr-Brown IVC 102 Precision Switched Integrator Transimpedance Amplifier; Printed Jun. 1996.
125-MHz & 1-GHz Photoreceivers; pp. 110-111.
OSI Optoelectronics; Photodiode Characteristics and Applications; pp. 2-7; www.osioptoelectronics.com.
International Search Report and Written Opinion; PCT/US2011/064562; Apr. 6, 2012, 11 pages.

* cited by examiner

*Primary Examiner* — Christine Sung

(74) *Attorney, Agent, or Firm* — Conley Rose, P.C.; Rodney B. Carroll

(57) ABSTRACT

A light source is gated ON and OFF in response to a pulsed signal. Photo emissions from the light source are coupled to a material under test. Resonant fluorescent emissions from the material are coupled to a photodiode. Current from the photodiode is coupled into an amplifier system comprising a first and second amplifier stages. The first amplifier stage is gated to a low gain when the light source is turned ON and the gain is increased when the light source goes from ON to OFF. The second amplifier stage has digitally programmable offset and gain settings in response to control signals. The output of the second amplifier stage is digitized by an analog to digital converter. A controller generates the pulse control signal and the control signals.

20 Claims, 6 Drawing Sheets

FLUORESCENCE EMISSIONS DETECTOR

TECHNICAL FIELD

This invention relates to operating an excitation source and analog front end of a fluorescence emissions detection circuit.

BACKGROUND INFORMATION

Fluorescence is the emission of electromagnetic radiation or light immediately after absorbing incident radiation or light. A resonant fluorescence phenomenon occurs when the spectra or wavelength of the emission overlaps the incident or excitation source wavelength. The delay time between absorption and emission is minimal. The fluorescence lifetime or 1/e value is the time that is equivalent to 36.8% of the initial intensity value of the fluorescing signal.

Detecting fluorescence requires receiving the fluorescence emission by a photo sensitive device, converting it to an electrical signal, and amplifying the resulting electrical signal. The spectral power density (SPD) of the excitation source is multiple orders of magnitude higher than the SPD of the emission from the fluorescing material. Because of this, crosstalk in a detection system is an undesired effect of overlapping spectra. A saturated amplifier can substantially degrade the bandwidth and linearity of the system when detecting fluorescence in materials where the fluorescence has a short lifetime.

A current analog of the fluorescing emission, as measured in a detection system, may be represented by an exponential equation:

$$f(t)=A+B_1(e^{-t/\tau 1})+B_2(e^{-t/\tau 2}) \qquad (1)$$

In this equation (1), "A" represents a constant background signal such as photodiode dark current or electrical noise or offsets. The coefficients $B_1$ and $B_2$ represent initial emission intensities and the exponents represent the time constants of individual components in the composite emission signal as a function of time, t.

It is desirable to accurately detect resonant fluorescence emission signals with time constant components ranging from 10 to 1000 microseconds. A desired output signal is a decaying exponential voltage that is the analog of a resonant fluorescence signal with minimal distortion due to instrumental artifacts and overlapping spectra. It is also desirable to have a light excitation source such as a single light emitting diode (LED) or multiple LEDs with sufficient power and a sufficiently short duration or pulse width. It is also desirable to have a driver for the light source that is compatible with CMOS logic levels such that a single general purpose I/O pin from a microcontroller or DSP can control the turn-ON and turn-OFF timing of the LED.

There is a desire for a resonant fluorescence detection system that is simple, reliable, low cost, and able to be configured with high volume LED light sources and photodiode detectors. It is further desirable to have digitally controlled gain, offset, and gating to prevent amplifier saturation and non-linearity in addition to enabling the normalization of detector performance to reduce device to device variance for a wide variety of applications including variances in taggant loading, which may result in lower or higher emission intensity.

SUMMARY

Aspects of the present invention detect resonant fluorescent emissions from a test material employing a pulsed light source that is gated ON and OFF with a pulsed control signal. The light pulse is coupled into the material under test. Resonant fluorescence emissions from the test material are coupled into a photodiode that converts the radiation to an electrical current. The current is amplified in an amplifier system, which may comprise first and second stage amplifiers. The first stage amplifier may be a current-to-voltage converter. The gain of the first amplifier stage is reduced when the light source is gated ON and increased when the light source is gated OFF. The source impedances on the inputs of the first stage amplifier are balanced so the effective input resistance and capacitance are substantially the same when the amplifier is switched between low gain and high gain to minimize effects of charge injection from the switches on the amplifier response time. The output of the first amplifier is coupled to the second stage amplifier which may have programmable offset and gain digitally controlled in response to control signals. The output of the second stage may be digitized by an analog-to-digital converter and analyzed. The pulse control signal and the amplifier control signals may be generated by a controller.

DETAILED DESCRIPTION

The analog front end of a single element resonant fluorescence detection system comprises an excitation circuit and a single photodiode connected to a photodiode amplifier. The analog front end (AFE) establishes a maximum performance of the system with regards to bandwidth, signal-to-noise ratio, linearity, and dynamic range. The output comprises a decaying exponential voltage that is the analog of a resonant fluorescence signal with minimal distortion due to instrumental artifacts and overlapping spectra.

Fluorescence is the emission of electromagnetic radiation or light immediately after absorbing incident radiation or light. The resonant fluorescence phenomenon occurs when the spectra or wavelength of the emission overlaps the incident or excitation source wavelength. The delay time between absorption and emission is minimal. The fluorescence lifetime or 1/e value is the time that is equivalent to 36.8% of the initial intensity value of the fluorescing signal.

The excitation circuit is designed to drive a single light emitting diode (LED), or multiple LEDs, with sufficient power and with a sufficiently short duration or pulse width. The input of the excitation circuit may be designed to be compatible with CMOS logic levels such that a single general purpose I/O pin from a microcontroller or DSP may control the turn-ON and turn-OFF timing of the LED. A typical excitation pulse width may be in the range of 1 millisecond.

A photodiode is biased to operate in the photoconductive mode and connected to a two-stage amplifier. The first stage amplifier may be a transimpedance amplifier designed to convert the photodiode current to a voltage. The second stage amplifier may be a non-inverting amplifier that further amplifies and conditions the photodiode current.

The digital input signal to the excitation circuit also drives or gates analog switches, which substantially reduces the gain of the transimpedance amplifier when the excitation LED is ON or radiating. Reducing amplifier gain as a function of excitation source status decreases non-linearity due to amplifier saturation or cross-talk from the excitation source, crosstalk being an undesired effect of overlapping spectra. The spectral power density (SPD) of the excitation source is multiple orders of magnitude higher than the SPD of the fluorescing material emission. A saturated amplifier may substantially degrade the bandwidth and linearity of the system when detecting materials with short lifetimes, thus impairing, complicating or increasing cost of authentication system and method. Further details are described relative to the figures that follow.

Figure 1:
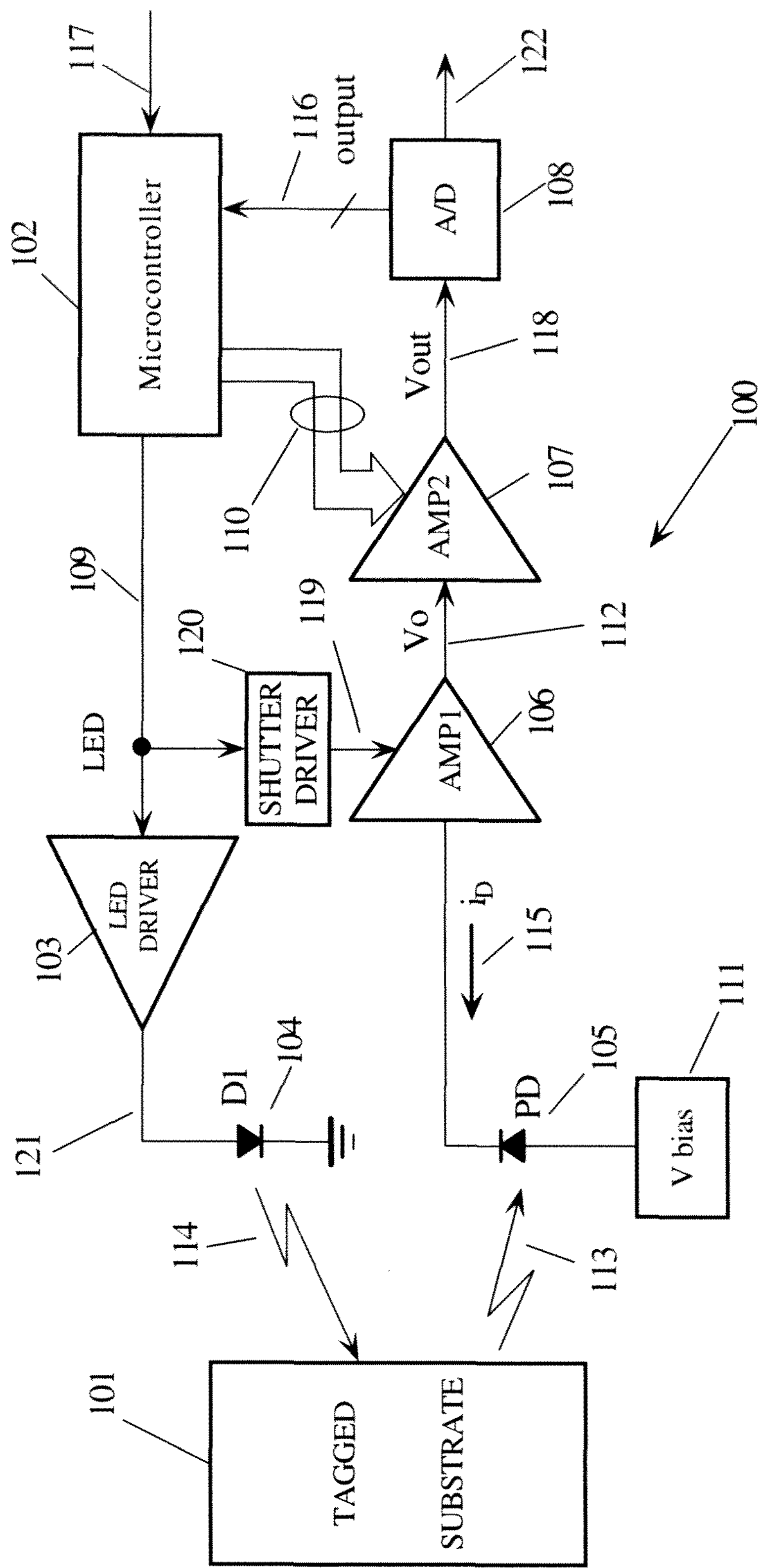
FIG. 1 illustrates a system block diagram of a resonant fluorescence emissions detection system.

FIG. 1 illustrates a block diagram of resonant fluorescence detection system 100. System 100 may be utilized to determine if a monitored material possesses a particular taggant which is configured with a composition that fluoresces when irradiated with a particular wavelength of light. Microcontroller 102, in response to control steps programmed within, provides a pulsed signal 109 with a predetermined pulse width (e.g., 1 millisecond) to light emitting diode (LED) driver 103. LED driver 103 is configured to turn ON LED 104 (pulse signal 121) for a time period equal to the predetermined pulse width. When LED 104 turns ON, a pulse of light 114 excites tagged substrate 101 (an example of the aforementioned material possessing a taggant). In response to the pulse of light 114, tagged substrate 101 fluoresces after absorbing the incident light 114, thereby producing resonant fluorescence emission 113. Photodiode (PD) 105 is configured as a photoconductive detector. Bias voltage (V bias) 111 reverse biases PD 105. When no light is received by PD 105, it conducts "dark current" under the influence of bias voltage 111. When light (e.g., 113) impinges on PD 105 it is rendered more conductive and signal current 115, proportional to the incident light 113, flows through transimpedance amplifier (AMP1) 106, which converts current 115 to output voltage Vo 112. Output voltage Vo 112 is further amplified by amplifier (AMP2) 107, thus producing output voltage Vout 118. Analog-to-digital (A/D) converter 108 converts Vout 118 to a digital signal at output 122. A/D converter 108 may also be coupled to microcontroller 102 via signal(s) 116. Microcontroller 102 receives program signals 117 and provides signal 109 and control signals 110. Control signals 110 provide digital signals used to affect offset control and gain control for amplifier 107. Pulse signal 109 is used to gate LED driver 103 and shutter driver 120. Shutter driver 120 is used via voltage-controlled analog switches within amplifier 106 (see FIG. 2), to switch resistors that balance the source impedances of amplifier 106 when it is switched between a high and low gain.

Figure 2:
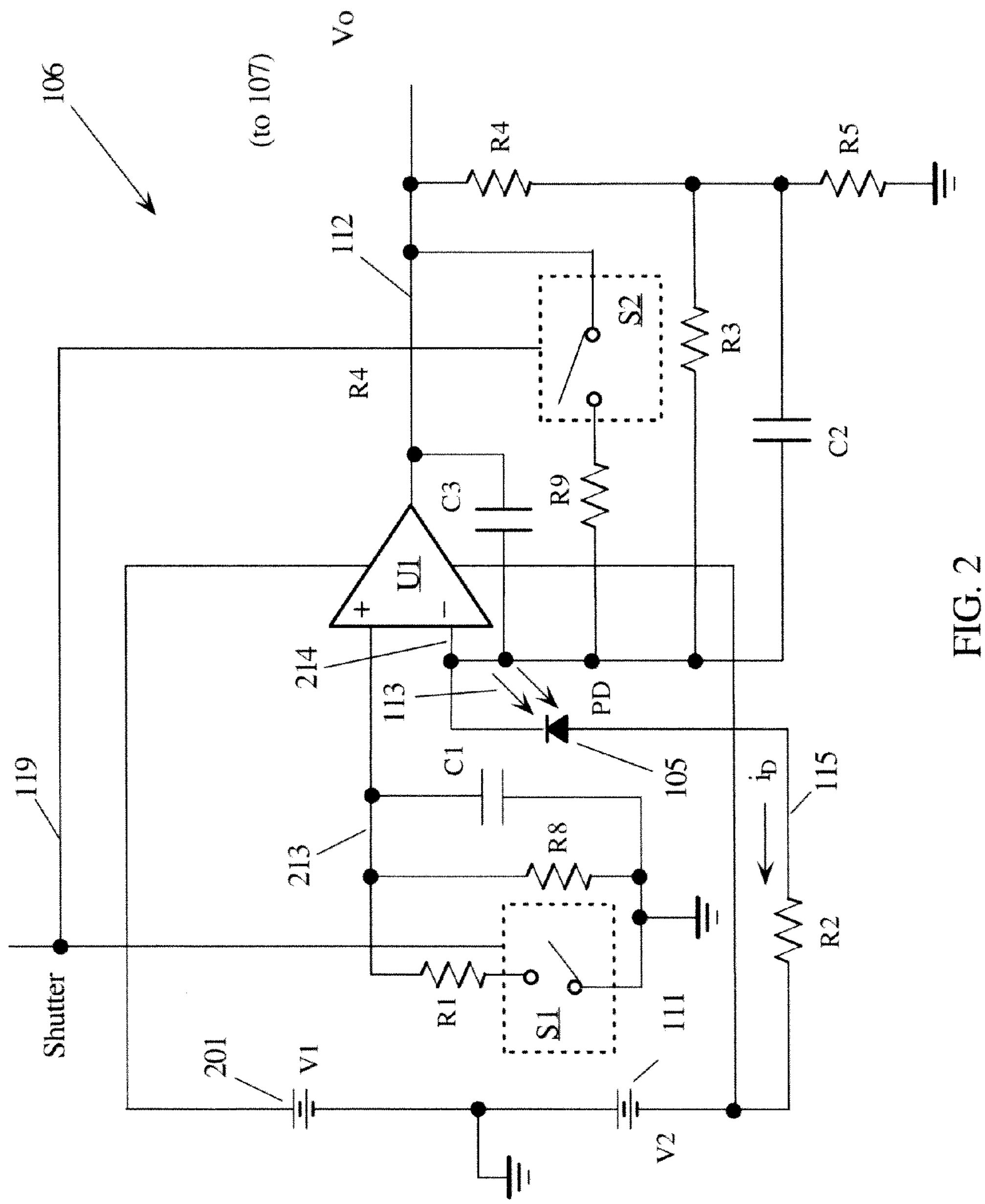
FIG. 2 illustrates a circuit diagram of a first stage transconductance amplifier.

FIG. 2 illustrates further details of amplifier 106. Amplifier 106 comprises operational amplifier U1 as a main gain element. Amplifier U1 is powered by positive voltage V1 201 and previously disclosed negative bias voltage V2 111. An operational amplifier, such as U1, is designed to have a very high input impedance at its input terminals (e.g., 213 and 214) and a very high open loop gain. External feedback components are used to provide the performance desired in amplifier 106. As previously described, PD 105 is reversed biased, and substantially all of the current flow (i.e., current 115) through PD 105 is forced to flow through the feedback network, comprising analog switch S2, resistor R9, resistor R3, capacitor C2, and resistors R5 and R4, by action of amplifier output voltage Vo 112. Because of the high gain between the inputs 213, 214 of amplifier U1, amplifier output voltage Vo 112 "servos" to a value necessary to maintain the voltage difference between input 213 and input 214 at essentially zero volts. The high input impedance of negative input 214 assures essentially all of the current 115 flows into the aforementioned feedback network.

Since PD 105 is reversed biased, it acts much as a current source, wherein the magnitude of current that flows (i.e., current 115) depends predominately on the amount of light energy 113 impinging on PD 105, and does not depend significantly on resistor R2 or bias voltage 111.

Resistors R3, R4, R9, and R5 shape the gain and, along with capacitors C2 and C3, the frequency response of amplifier 106. It can be shown that the transfer function, expressed as the ratio (Vo 112/current 115), is equal to (R4+R3(1+R4/R5)) when resistor R9 is selected by switch S2. The resistance of resistor R9 is much smaller than the resistances of resistors R3, R5, or R3. When resistor R9 is selected, essentially all of current 115 flows in resistor R9, and the aforementioned transfer function is essentially equal to the value of resistor R9. Thus, switching in resistor R9 when LED 104 is pulsed ON reduces the gain of amplifier 106. Capacitor C2 is in parallel with resistor R3 and reduces the gain of amplifier 106 as frequency increases when switch S2 is normally open. Reducing the gain of amplifier 106 during the time LED 104 is pulsed ON prevents, or at least reduces, saturation or cross-talk, since the spectral power density (SPD) of LED 104 is multiple orders of magnitude greater than the SPD of resonant fluorescence emissions 113.

Switches S1 and S2 may be electronic switches, which may cause charge injection at the inputs of amplifier U1 when switching amplifier 106 between a high and low gain. If different source impedances are presented at the inputs when the gain is switched, switches S1 and S2 may thereby cause amplifier 106 to have an increased settling time. Capacitances C1 and C2 are thereby sized to be substantially equal. Capacitor C3 provides compensation for gain peaking, thus improving amplifier stability. Likewise, resistances R8 and R3 are sized to be substantially equal, and switched resistances R9 and R1 are sized to be substantially equal. Balancing the impedances at the input of amplifier U1 improves system performance when amplifier U1 is switched between high gain and low gain when LED 104 is gated ON and OFF.

Figure 3A:
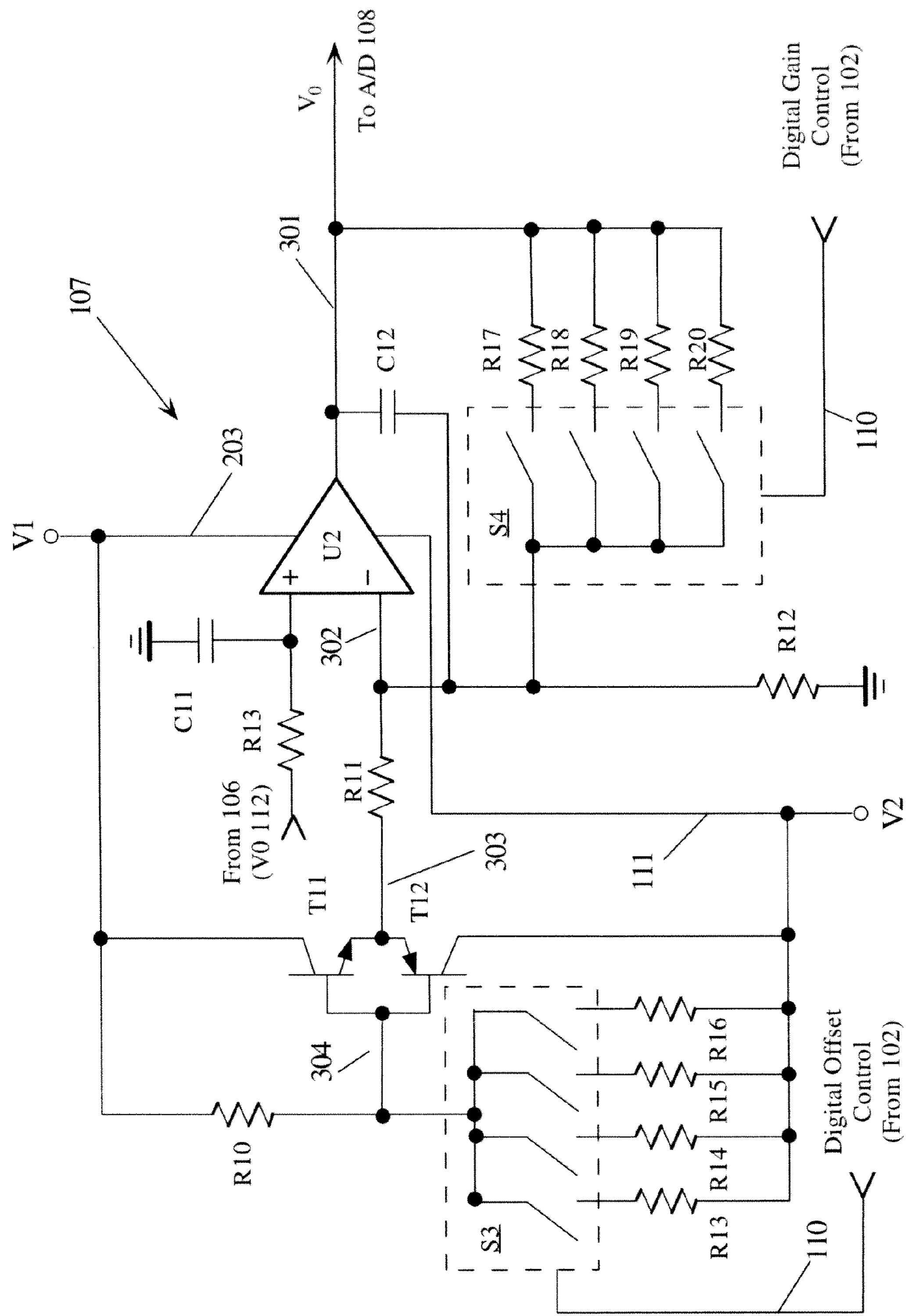
FIG. 3A illustrates a circuit diagram of one embodiment of a second stage amplifier with adjustable gain and offset.

FIG. 3A illustrates details of one embodiment of amplifier 107, which receives output voltage Vo 112 of amplifier 106. Amplifier 107 comprises operational amplifier U2 configured as a non-inverting amplifier with a gain set by feedback resistors R17-R20 and R12. The closed loop gain of amplifier 107 may be shown to be greater than one and equal to the sum of resistor R12 and selected resistor(s) from R17-R20 divided by resistor R12. If analog switch S4 selects more than one resistor, then the resistor value used in the gain equation is the parallel combination of the selected resistors. Analog switch S4 acts to provide programmable gain in response to digital gain control signals 110 from control logic circuitry 102 (see FIG. 1). Amplifier 106 will undoubtedly have a DC offset component in its output Vo 112 that it is undesirable. By applying a DC signal to one end of resistor R11 (signal 303), the offset, as seen in output Vo 118, may be controlled to a desired value. FIG. 3A illustrates an embodiment where the offset signal 304 is provided by a programmable voltage divider network comprising resistors R10 and R13-R16 and switch S3, which may be an analog switch. Transistors T11 and T12 are configured to receive offset signal 304 and provide a voltage follower whose output (303) voltage will go from positive to negative to facilitate a bipolar offset voltage. Other circuitry for generating the compensating offset voltage to node 303 may be used and still be within the scope of the present invention. Capacitors C11 and C12 reduce the high frequency gain of amplifier 107, which may enhance the overall signal-to-noise ratio of the detector in the bandwidth of interest.

Figure 3B:
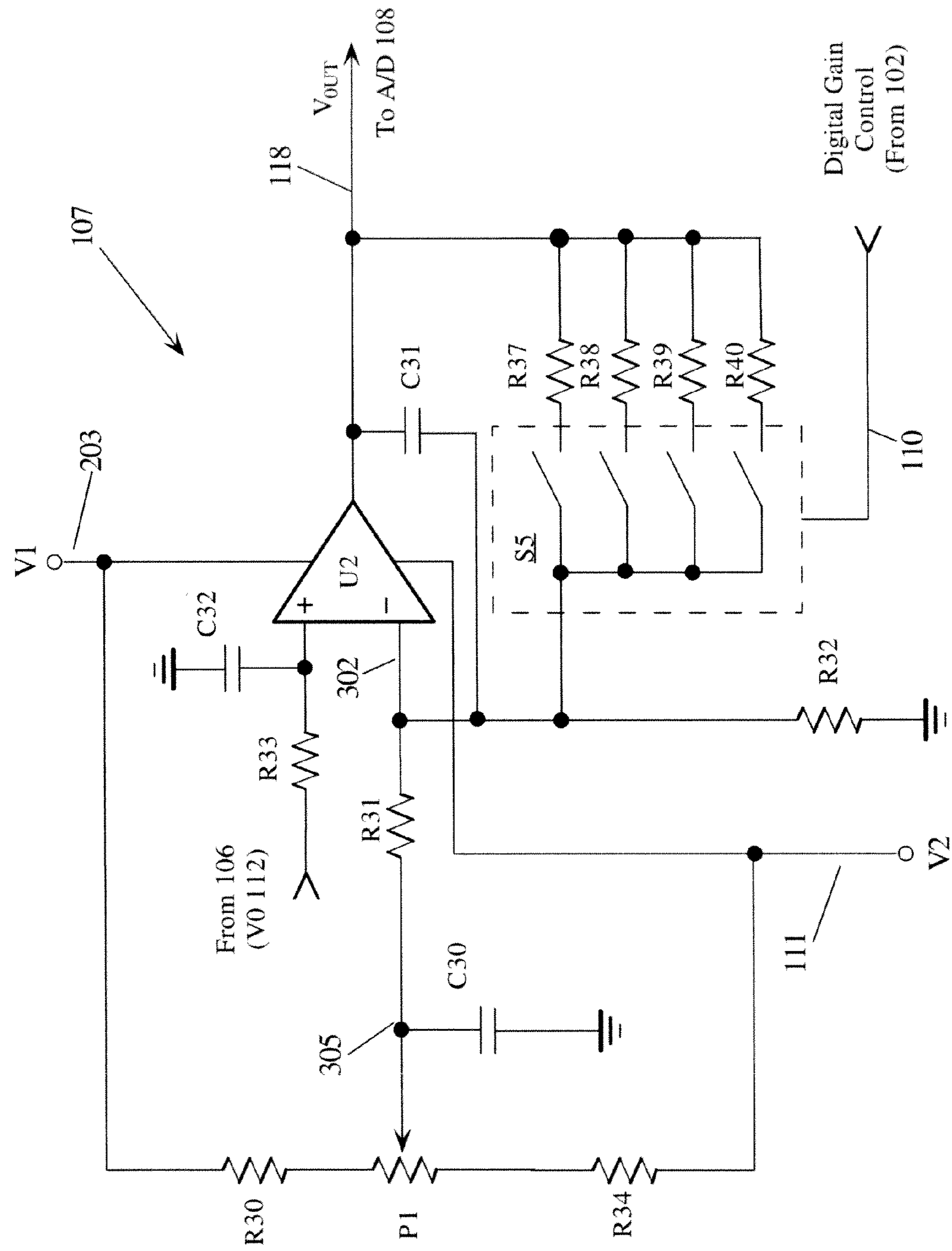
FIG. 3B illustrates a circuit diagram of another embodiment of a second stage amplifier with programmable gain and offset.

FIG. 3B illustrates details of another embodiment for an amplifier 107, which receives output voltage Vo 112 of amplifier 106. Amplifier 107 comprises operational amplifier U2 configured as a non-inverting amplifier with a gain set by feedback resistors R37-R40 and R32. The closed loop gain of amplifier 107 may be shown to be greater than one and equal to the sum of resistor R32 and selected resistor(s) from R37-R40 divided by R32. If switch S5 which may be an analog switch selects more than one resistor, then the resistor value used in the gain equation is the parallel combination of the selected resistors. Switch S5 acts to provide programmable gain in response to digital gain control signals 110 from control logic circuitry 102 (see FIG. 1). Amplifier 106 will undoubtedly have a DC offset component in its output Vo 112 that it is undesirable. By applying a DC signal to one end of resistor R31 (signal 305), the offset, as seen in output Vo 118, may be reduced to a small value. FIG. 3B illustrates an embodiment where the offset signal 305 is provided by a voltage divider network comprising resistors R30 and R34 and potentiometer P1. Resistors R30 and R34 set the coarse division and potentiometer P1 provides for fine adjustment of an offset voltage plus and minus around zero volts. It is understood that programmable switch S5 may be replaced by manual switches for selecting resistors R37-R40.

Figure 4:
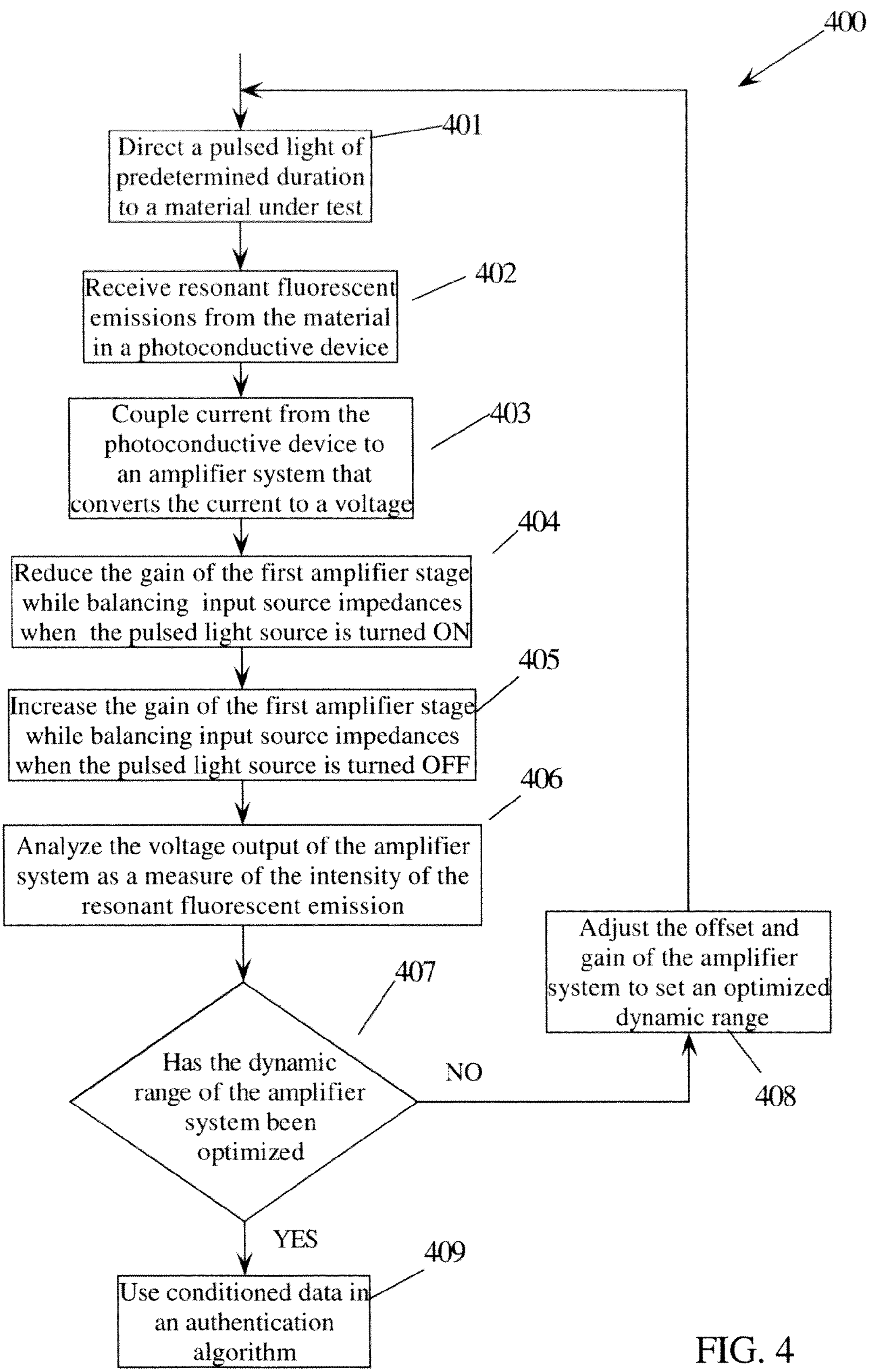
FIG. 4 illustrates a flow diagram of method steps according to embodiments herein.

FIG. 4 illustrates a flow diagram of method steps 400 according to aspects of the present invention. In step 401, a pulsed light 114 of predetermined duration is directed to the material under test 101. In step 402, resonant fluorescence emissions 113 from the material 101 are received by a photoconductive device 105. In step 403, the photoconductive device's current 115 is modulated by the resonant fluorescence emissions 113 and coupled to an amplifier system, comprising amplifiers 106 and 107, which converts the current changes to voltage changes. In step 404, the gain of the first amplifier stage 106 is reduced and its input source impedances are balanced during turn ON of the pulsed light source LED 104. In step 405, the gain of the first amplifier stage 106 is increased and its input source impedances are balanced during turn OFF of the pulsed light source LED 104. In step 406, the output waveform of the second amplifier stage 107 is analyzed as a measure of the intensity of the resonant fluorescence emission.

In step 407, a test is done to determine if the dynamic range of the amplifier system has been optimized. If the dynamic range has not been optimized in step 408, the offset and gain of the amplifier system are adjusted to set an optimized dynamic range. If it is determined in step 404 that the dynamic range of the amplifier system has been optimized, then in step 409 the waveform from the amplifier system is conditioned and used in an authentication algorithm validating the material under test.

Figure 5:
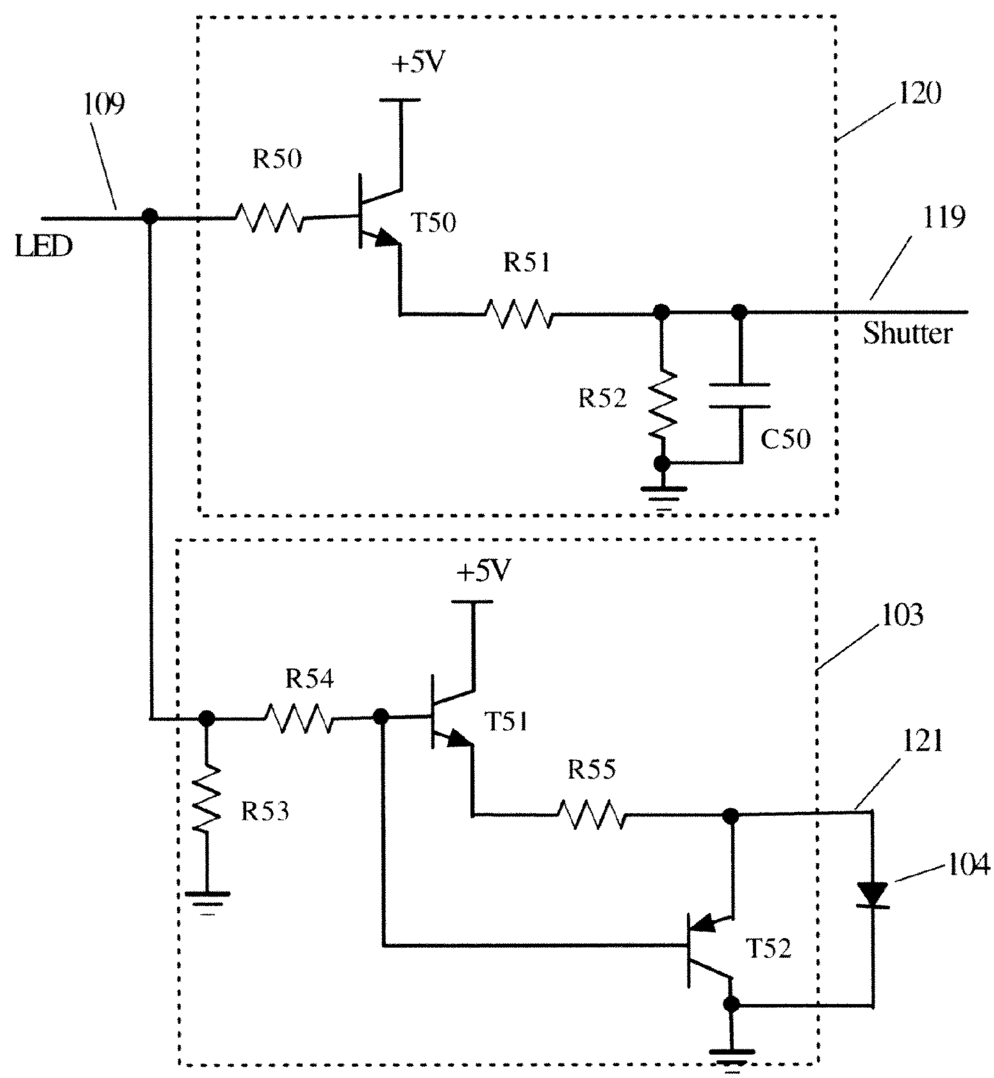
FIG. 5 illustrates a circuit diagram of an LED driver and an electronic switch driver useable with embodiments herein.

FIG. 5 illustrates a circuit diagram of a LED driver 103 and a shutter driver 120 useable with embodiments herewithin. Shutter driver 120 receives a pulse signal 109 from microcontroller 102. Shutter signal 119 may be used to turn ON switches S1 and S2 (see FIG. 2) from their normally open state, thereby coupling resistor R1 to ground and coupling resistor R9 between the output 112 and the input 214 of amplifier U1. Shutter signal 119 may have a rise time (essentially determined by resistor R51 and capacitor C50) different from its fall time (essentially determined by resistor R52 and capacitor C50). The rise time determines how fast amplifier 106 switches to low gain when LED 104 is turned ON and the fall time determines how quickly the gain of the amplifier is switched to a high gain after LED 104 is turned OFF. Resistor R50 limits the base current to transistor T50.

LED driver 103 may be used to generate drive signal 121 that turns ON and OFF exemplary LED 104. Transistor T51 provides the drive current to LED 104 through resistor R55 when LED signal 109 is at a positive level reducing the loading on LED signal 109. Since the source impedance of transistor T51 and the resistance of resistor R55 are low, the turn ON time of LED 104 is fast. When LED signal 109 goes low to turn OFF LED 104, the capacitance of LED 104 would slow its turn OFF if transistor T52 was not present. When LED signal 109 goes low, transistor T52 will turn ON, providing a low impedance discharge path (between its emitter and collector) for the signal 121 until its value drops below the emitter-to-base turn ON threshold of transistor T52. Turning LED 104 OFF quickly reduces the delay time required before the fluorescence emission signal is ready for analysis.

Returning to FIG. 1, an application of system 100 is to provide a signal from objects possessing a particular taggant for purposes of identification. For example, tagged substrate 101 may be an item of value or critical source of information such as labels, product packaging material, a bank note or a series of bank notes that pass by system 100 on a conveyor system (not shown) during manufacturing, warehousing, sorting, or retail operations. Tagged items may also include coins, stamps, and consumable medical supplies, such as reagent and glucose test strips that are targeted by counterfeiting operations or unlicensed third party manufacturing operations. As each bank note or tagged item passes by the optical components 104 and 105, system 100 is programmed to pulse LED 104. This may be performed by a communication 117 from the conveyor system, or a proximity detector such as a photointerruptor with an output conditioned to be provided to control logic 103 when each bank note is within the target area of the optical devices 104, 105. If a particular bank note possesses the specified and known taggant, it will fluoresce when irradiated by light 114, and PD 105 will then detect that florescence 113, eventually resulting in output 114 indicating the presence of the taggant. In such a system, one or more bank notes may be "scanned" and each determined to be either authentic or counterfeit. System 100 provides advantages such that this authentication process may be performed faster (the conveyor speed may be increased) while maintaining a desired level of accuracy. It is understood that any material or device with a fluorescing taggant may be monitored with such a system 100.

One of ordinary skill in the art will appreciate other advantages of the embodiments described herein. Embodiments of the invention do not require optical components such as lens and optical filters to improve the signal-to-noise ratio of the emission signal or to isolate the photodiode from the excitation source when it is active, thus the increasing cost and form factor of the detector.

A single digital signal or bit may be used to turn the excitation source ON and OFF while also controlling the gain of the first stage amplifier using a method that minimizes amplifier settling time due to balancing the effective charge injection of the pair of analog switches. Embodiments herein do not rely on non-linear amplifier functions, and the photodiode bias circuit does not require a voltage clamp to maintain desired performance.

The effective dynamic range of the invention is sufficient with amplifier power supply rail voltages as low as +/−5 VDC. Operating from low power supply rail voltages and reduced power enables a low noise design that may be powered from existing power supply nodes contained within a host system. For example, all power to operate a device inclusive of the invention and an embedded system host may be derived from a universal serial bus (USB) port. The USB port contains a +5 VDC power source. This source may be converted to −5 VDC using an integrated circuit (not shown) designed to function as a voltage inverter or charge pump.

Distributing the overall amplifier gain in two stages enables embodiments to have a faster sensor response time due to a lower measurement time constant affected by the photodiode capacitance. The photodiode appears as a current source in parallel with a capacitor. While increasing the reverse bias reduces the capacitance of the photodiode, it is desirable to keep the voltage supplies (thus bias voltage) low. Using a low gain first stage allows the resistances of the feedback to be smaller, and thus the time constant of the response time for a given photodiode capacitance may be reduced or minimized. The first stage gain (transimpedance) may be lower while the second stage gain may be higher.

The direct current (DC) offset value referenced by "A" in equation (1) may be substantially eliminated in embodiments herein by adding the level shifting circuit to the second stage amplifier without increasing the response time which is determined by the impedances of the first amplifier stage and the photodiode capacitance.

The second stage amplifier in embodiments is a programmable gain non-inverting amplifier with a resistor ladder to the operational amplifier negative feedback. Having a programmable gain amplifier enables an automatic gain selection algorithm to substantially extend an overall dynamic range of the system. The second stage amplifier may also include a programmable offset compensation circuit (digital potentiometer). The offset circuit may be adjusted to ensure that the analog output signal remains above ground potential. The effects of the programmable offset circuit may be integrated into an automatic gain algorithm to further maximize dynamic range for a broad set of operating conditions. The second stage may also include an active filter (e.g., capacitor C12 in FIG. 3A) to selectively attenuate or filter targeted frequency bands without affecting the bandwidth of the photodiode sensor. The transient response of the system to a unit step function in embodiments is reduced by balancing the source impedances at the inputs of the first stage amplifier that uses analog switches to switch between a high and low gain.

What is claimed is:

1. A system for detecting resonant fluorescence comprising:

a light emitting diode (LED) configured to emit pulsed photoemissions towards a target in response to a pulsed signal;

a photodiode configured to (1) receive resonant fluorescence emissions from the target, the resonant fluorescence emissions a response to the pulsed photoemissions, and (2) generate a current in response to the received resonant fluorescence emissions; and an amplifier system having first and second stages, wherein the first stage is configured to receive (1) the current from the photodiode, and (2) a gating signal as a function of the pulsed signal, the first stage further configured so that the gating signal gates the first stage to have a first output with (1) a first gain when the LED is activated to emit one of the pulsed photoemissions, and (2) a second gain when the LED is deactivated, wherein the second stage is configured to receive control signals and the first output of the first stage, the second stage having a second output and having a gain and offset configured to respond to the control signals to produce a linear dynamic range for a signal at the second output of the second stage that is an analog of the resonant fluorescence emissions from the target.

2. The system of claim 1 further comprising a controller programmed to generate the pulsed signal and the control signals.

3. The system of claim 1 further comprising an analog-to-digital converter for digitizing the second output of the second stage.

4. The system of claim 1, wherein the first stage comprises a transimpedance amplifier receiving the current and generating a voltage proportional to the current.

5. The system of claim 4, wherein the first stage comprises a first operational amplifier having a positive input selectively coupled to a ground potential through a first resistor/capacitor network setting a first input source impedance, the photodiode coupled between a negative input of the first operational amplifier and a supply voltage, and a second resistor/capacitor network selectively coupled from the negative input to an output of the first operational amplifier setting the first gain of the first stage and a second input source impedance.

6. The system of claim 5, wherein a first analog switch selectively couples resistors of the first resistor/capacitor network to the positive input of the first operational amplifier in response to the pulsed signal.

7. The system of claim 5, wherein a second analog switch selectively couples resistors of the second resistor/capacitor network to the negative input of the first operational amplifier in response to the pulsed signal thereby decreasing the first gain during stimulated emissions from the LED and increasing the first gain during resonance fluorescence emissions from the target.

8. The system of claim 1, wherein the second stage comprises a second operational amplifier having a positive input coupled to the first output of the first stage, a negative input coupled through a first resistor to an offset voltage and a three terminal voltage divider network including selectively coupled parallel resistors connected in series with a single resistor, one terminal of the voltage divider network is coupled to the second output of the second stage, a second terminal of the voltage divider network is coupled to a ground potential and a third terminal of the voltage divider network is coupled to the negative input of the second operational amplifier.

9. The system of claim 8, wherein the parallel resistor network comprises analog switches for selectively connecting resistors of the parallel resistor network to the negative terminal of the second operational amplifier, the analog switches selectable in response to the control signals.

10. The system of claim 8 further comprising an analog-to-digital converter having an input coupled to the second output of the second stage and digital outputs generating a digital signal.

11. The system of claim 8 further comprising a programmable offset voltage generator having an output generating the offset voltage in response to the control signals.

12. The system of claim 6, wherein the resistors are selectively connected in parallel with the capacitor in first resistor/capacitor network in response to the control signals and the values of the resistors and capacitor are sized to minimize the differences in impedances seen by charge injection at the inputs of the first operational amplifier when the gain of the first amplifier stage is gated by the pulse signal thus minimizing response time of the system.

13. The system of claim 12, wherein the output of the offset generator is isolated from the first resistor with a low output impedance buffer stage.

14. The system of claim 8, wherein the offset generator is programmed with parallel resistor network selectively connected in a voltage divider network in response to the control signals.

15. A method for detecting resonant fluorescent emissions from a target, comprising:

irradiating the target with light from a pulsed light source, thereby causing the target to emit resonant fluorescent emissions, the pulsed light source receiving a signal that activates and de-activates the pulsed light source to gate the light ON and OFF;

receiving the resonant fluorescent emissions from the target by a photoconductor to thereby produce a current modulated by the received resonant fluorescent emissions;

coupling the current from the photoconductor to an amplifier system comprising a first stage amplifier that converts the current to a voltage output and a second stage amplifier with programmable gain and offset that receives the voltage output and produces an amplifier output;

reducing a gain and balancing source impedances of the first stage amplifier in response to the signal that activates the pulsed light source ON; and increasing the gain and balancing source impedances of the first stage amplifier in response to the signal deactivating the pulsed light source from ON to OFF.

16. The method of claim 15 further comprising:

analyzing the amplifier output for cut-off and saturation;

optimizing a dynamic range of the amplifier system;

adjusting digitally the programmable gain of the second stage amplifier to optimize the dynamic range, and adjusting digitally the offset of the second stage amplifier to optimize the dynamic range.

17. The method of claim 16 further comprising converting the amplifier output to a digital signal using an analog-to-digital converter.

18. The method of claim 17, further comprising storing the digital signal in a controller as an analog of the resonant fluorescent emission.

19. The method of claim 15, wherein the photoconductor is a photodiode.

20. The method of claim 15, wherein the balancing of source impedances of the first stage amplifier minimizes a settling time of the amplifier system.

* * * * *